(12) United States Patent
Erez et al.

(10) Patent No.: US 11,697,006 B2
(45) Date of Patent: Jul. 11, 2023

(54) POWDER DISPENSING APPLICATOR

(71) Applicant: Omrix Biopharmaceuticals Ltd., Rehovot (IL)

(72) Inventors: Lior Erez, Shoham (IL); Erez Ilan, Kibbutz Netzer Sereni (IL); Omri Faingold, Rehovot (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 509 days.

(21) Appl. No.: 16/181,439

(22) Filed: Nov. 6, 2018

(65) Prior Publication Data

US 2019/0134366 A1    May 9, 2019

Related U.S. Application Data

(60) Provisional application No. 62/583,017, filed on Nov. 8, 2017.

(30) Foreign Application Priority Data

Nov. 8, 2017  (IL) .......................................... 255520

(51) Int. Cl.
*A61M 35/00*    (2006.01)
*A61M 11/00*    (2006.01)

(52) U.S. Cl.
CPC ........ *A61M 35/003* (2013.01); *A61M 11/008* (2014.02); *A61M 2202/064* (2013.01); *A61M 2205/0266* (2013.01); *A61M 2205/7536* (2013.01); *A61M 2206/20* (2013.01)

(58) Field of Classification Search
CPC .. A61M 35/003; A61M 35/30; A61M 11/008; A61M 11/02; A61M 2206/20; A61M 2206/064; A61M 2205/7536; A61M 2202/064; A61M 5/3015; A61M 2205/0266

See application file for complete search history.

(56) References Cited

U.S. PATENT DOCUMENTS

| | | | |
|---|---|---|---|
| 9,205,240 B2 | 12/2015 | Greenhalgh et al. | |
| 2002/0092523 A1 | 7/2002 | Connelly | |
| 2004/0050885 A1* | 3/2004 | Stradella ........... | A61M 15/0028 222/633 |
| 2014/0076315 A1* | 3/2014 | Von Schuckmann ....................... | A61M 15/0063 128/203.15 |
| 2016/0074602 A1 | 3/2016 | Wang et al. | |
| 2016/0167071 A1* | 6/2016 | Baillet ................... | B05B 11/06 222/23 |

(Continued)

FOREIGN PATENT DOCUMENTS

| | | |
|---|---|---|
| FR | 3007991 A1 | 7/2013 |
| WO | WO 92/06727 | 4/1992 |

(Continued)

OTHER PUBLICATIONS

International Search Report dated Mar. 6, 2019 for PCT/IL2018/000008.

*Primary Examiner* — Jessica Arble
(74) *Attorney, Agent, or Firm* — David R. Crichton

(57) ABSTRACT

Provided is an applicator for the dispensing of a powder such as a pharmaceutical powder, on a target location. Also, provided are methods of applying a powder on a surface using the applicator.

10 Claims, 8 Drawing Sheets

(56) References Cited

U.S. PATENT DOCUMENTS

2016/0375202 A1* 12/2016 Goodman ............ A61M 11/007
                                                        604/500
2018/0326166 A1* 11/2018 Von Schuckmann ........................
                                                        A61M 15/0065

FOREIGN PATENT DOCUMENTS

| WO | 94/11044 | 5/1994 |
|----|----------|--------|
| WO | WO 2013/122040 | 8/2013 |
| WO | 2016209442 A1 | 12/2016 |

* cited by examiner

POWDER DISPENSING APPLICATOR

TECHNOLOGICAL FIELD

The presently disclosed subject matter relates to an applicator for the dispensing of a powder such as a pharmaceutical powder, on a target location.

BACKGROUND

Examples of applicators of the kind to which the presently disclosed subject matter refers, are disclosed in U.S. Pat. No. 9,205,240, WO 92/06727, WO 2013/122040, US 2016/0074602 A1 and US 2016/0375202 A1.

U.S. Pat. No. 9,205,240 discloses a device for the topical dispensing of a powder, which uses a gas flow generator to cause gas to flow through the device and to entrain powder from a powder receptacle, while an agitator is used to mechanically agitate the powder receptacle to facilitate the release of powder from the powder receptacle.

WO 92/06727 discloses a disposable dispenser for a powder, in which the mechanism for powder release requires the penetration of membranes, which close two ends of a tubular powder magazine.

WO 2013/122040 A1 discloses a powder injection device, which injects pressurized gas, along with powder contained in a hopper, out of an exhaust pipe.

US 2016/0074602 A1 discloses a delivery device that provides co-delivery of a liquid medicament and a powder medicament onto a tissue or wound.

US 2016/0375202 A1 discloses a device for the expression of a hemostatic powder having an elongated reservoir with a manual air pump, such as a bellows, at a proximal end and an expression port at a distal end.

Acknowledgement of the above references herein is not to be inferred as meaning that these are in any way relevant to the patentability of the presently disclosed subject matter.

GENERAL DESCRIPTION

In accordance with one aspect of the presently disclosed subject matter, there is provided a powder dispensing applicator comprising:

a container having an inlet opening and an outlet opening spaced from each other along a longitudinal axis L of the applicator by a cavity configured to contain a powder therein at least in the vicinity of the outlet opening when the outlet opening is in a closed state and allows at least a part of the powder to be expelled therefrom when the outlet opening is in an open state;

an actuator comprising a deformable actuation element configured to contain a gas therein and to be brought from its initial state, in which it has a maximal operational volume, into a final state in which it has a minimal operational volume, via an intermediate state, in which it has an intermediate operational volume smaller than the maximal volume, for building up pressure in the applicator when the outlet opening is in its closed state; and further configured for being brought from its final state into its initial state by drawing ambient gas thereto from an exterior of the applicator after the built-up pressure is released; and a plug configured to obstruct the outlet opening for keeping it in the closed state until the plug is operated by the actuator to bring the outlet opening into the open state when the actuation element is brought from the intermediate state into the final state, to create a flow of the gas generated due to a pressure differential between that within the applicator and that at its exterior, for propelling therewith at least a portion of the powder out of the outlet opening in a pressurized burst.

The above structure of the applicator, and particularly, the fact that a pressure differential is built up within the applicator immediately prior to the outlet opening being brought into its open state, enables it to dispense powder in a pressurized burst without the use of an external pressurized gas source. Moreover, due to the above structure of the applicator, it can be configured so that, at each pressurized burst created thereby only a part of the powder (a single dose) is propelled from the container of the applicator, allowing thereby repeated dosage powder application. However, if desired, the applicator can be designed to dispense all the powder at once.

In some embodiments, the plug can be configured to be moved between an obstructing position, in which the outlet opening is closed thereby, and an unobstructing position, in which the plug is moved away from the outlet opening and is thus open.

In some embodiments, the outlet opening can be in the form of an axially extending passage having passage inner walls, in which the plug is disposed between the passage inner walls when in its obstructing position, and from which the plug is moved away from the passage inner walls into its unobstructing position.

In some embodiments, the actuator can be configured to selectively exert on the plug an opening force directed along the axis L to move the plug from the obstructing position into the unobstructing position; and a closing force directed along the axis to bring the plug into the obstructing position from the unobstructing position, when the opening force is terminated, and maintain it in this position until the opening force is exerted, one of the opening and closing forces being directed towards the cavity and the other one of these forces being directed away from cavity.

In some embodiments, the actuator can comprise at least one force transmitting element manipulatable, at least indirectly, by the deformable gas-containing actuation element, so as to exert the opening force to the plug when the deformable gas-containing actuation element is brought from the intermediate state into the final state.

In some embodiments, the actuator can comprise at least one force exerting element configured to manipulate, at least indirectly, the force transmitting element so as to exert the closing force on the plug when the deformable gas-containing actuation element is returned from its final state to its initial state. The force exerting element can have any appropriate structure. For example, it can be in the form of a spring, which is brought into a compressed state when the force transmitting element exerts the opening force on the plug to bring it into the unobstructing position, and an extended state, in which the force transmitting element exerts on the plug the closing force, to bring the plug into the obstructing position. Optionally, the spring can be configured to be maintained in its extended state until the deformable gas-containing actuation element is brought into the intermediate state from its initial state, and to be compressed at least indirectly by the deformable gas-containing actuation element when it is brought from the intermediate state into the final state.

In some embodiments, the deformable gas-containing actuation element can have a maximal amount of gas therein in the initial state when it has the maximal operational volume, and a minimal amount of gas therein in the final state when it has the minimal operational volume, and it can be sealingly connected to the container so as to introduce the gas into the cavity via the inlet opening along the axis L, when being brought from the initial state into the intermediate state, for building up pressure within the cavity when the outlet opening is in its closed state.

In some embodiments, the gas-containing actuation element can be configured to draw ambient air inside it at least partially via the outlet opening and the cavity, to increase its volume from the minimal operational volume to the maximal operational volume when it is returned from its final state to its initial state.

In some embodiments, the force exerting element can be configured so that the duration of time necessary for the force exerting element to cause the plug to be brought into its obstructing position from its unobstructing position is selected so as to allow the gas-containing actuation element to increase its volume from the minimal operational volume to at least the intermediate volume before the plug obstructs the outlet opening.

In some embodiments, the applicator can comprise at least one internal element disposed within the cavity of the container and configured to introduce turbulence into the flow of gas when propelling at least a portion of the powder. In some embodiments, the internal element can comprise at least one rib. Optionally, the rib can protrude inwardly from an inner wall of the container defining the cavity.

In some embodiments, the applicator can comprise a gas-permeable filter having a first side facing the inlet opening and a second side facing the outlet opening, and disposed in the cavity so as to create between the second side of the filter and the outlet opening a chamber for the powder, the filter being configured to form a barrier to the powder for preventing the powder from moving through the filter towards the inlet opening.

In accordance with another aspect of the presently disclosed subject matter, there is provided a powder dispensing applicator comprising a container having an inlet opening and an outlet opening spaced from each other by a cavity configured to contain a powder therein at least in the vicinity of the outlet opening; an actuator comprising a deformable gas-containing actuation element configured for building up pressure in the applicator when the outlet opening is in its closed state; and at least one internal element in the cavity configured to introduce turbulence into the gas when propelling at least a portion of the powder out of the outlet opening in a pressurized burst when the outlet opening is in the open state, by a flow of the gas generated due to a pressure differential between that within the applicator and that at its exterior.

The applicator according to this aspect of the presently disclosed subject matter can have any one or more of the features of the applicator according to the first aspect of the presently disclosed subject matter.

In accordance with a still further aspect of the presently disclosed subject matter, there is provided a method of applying a powder on a surface using a powder dispensing applicator comprising a container having an inlet opening and an outlet opening spaced from each other by a cavity configured to contain a powder therein, the method comprising:

pressurizing a gas contained in the applicator while maintaining the outlet opening closed;

subsequently opening the outlet opening to create a flow of the gas generated due to a pressure differential between that within the applicator and at its exterior, for propelling therewith at least a portion of the powder out of the outlet opening in a pressurized burst; and allowing drawing ambient gas into the applicator from its exterior after the built-up pressure is released.

The above method can enable the applicator used therein to dispense powder in a pressurized burst without the use of an external pressurized gas source. Moreover, the method can be configured so that, at each pressurized burst created therein only a part of the powder (a single dose) is propelled from the container of the applicator, allowing thereby repeated dosage powder application. However, if desired, the method can be used to dispense all the powder at once.

The applicator used in the method according to this aspect of the presently disclosed subject matter can be constituted by the applicator according to the first and/or second aspect of the presently disclosed subject matter.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

Figure 1A:
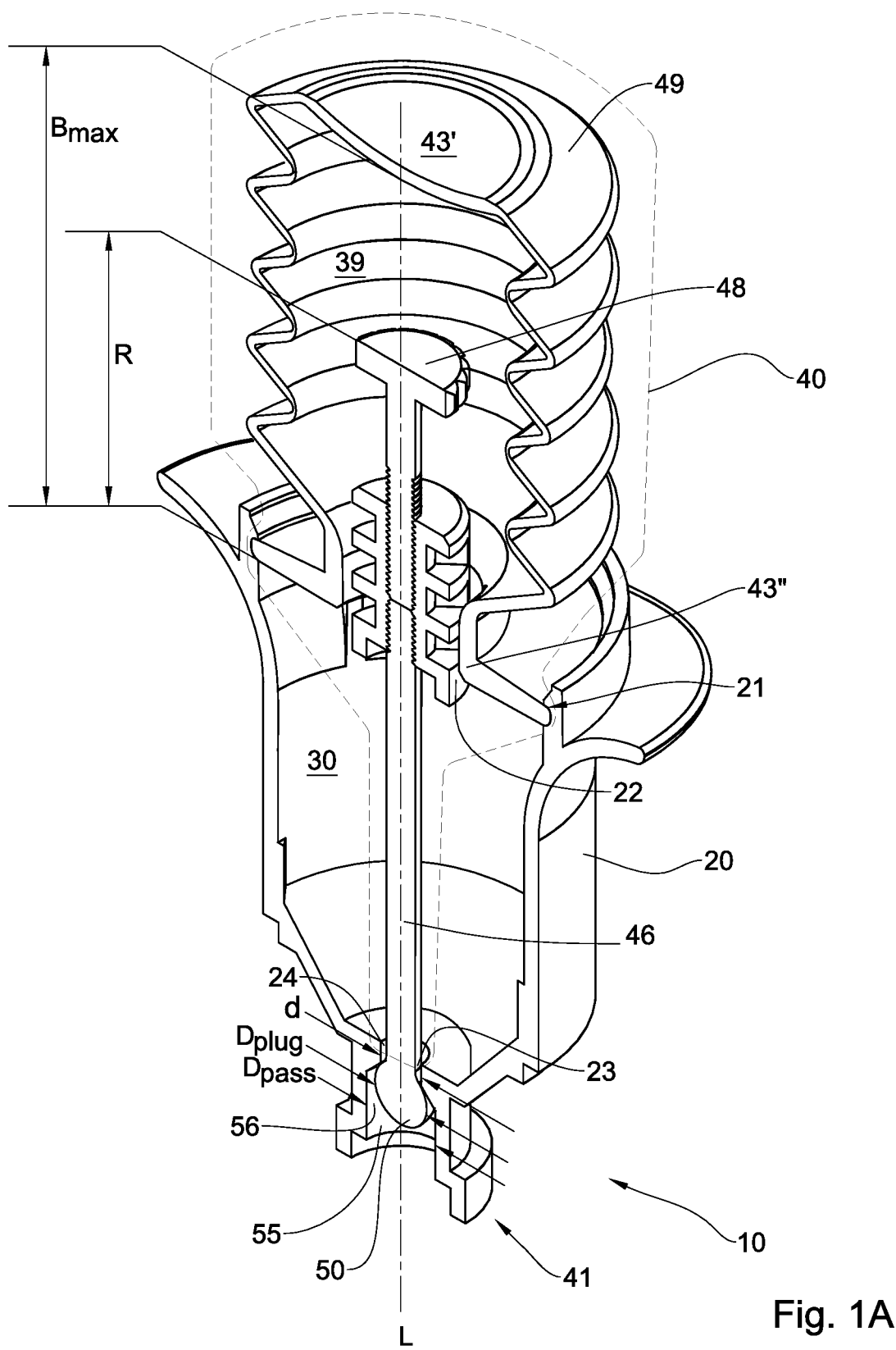
FIGS. 1A, 1B and 1C are schematic perspective illustrations of a powder dispensing applicator, in accordance with an example of the presently disclosed subject matter, with its deformable gas-containing actuation element in an initial, intermediate and final state, respectively.

It is noted that whether or not structural support and/or fastening elements are shown in the drawings, they should be assumed to be present and to be in the form of any suitable means known in the art.

DETAILED DESCRIPTION OF EMBODIMENTS

Figure 1B:
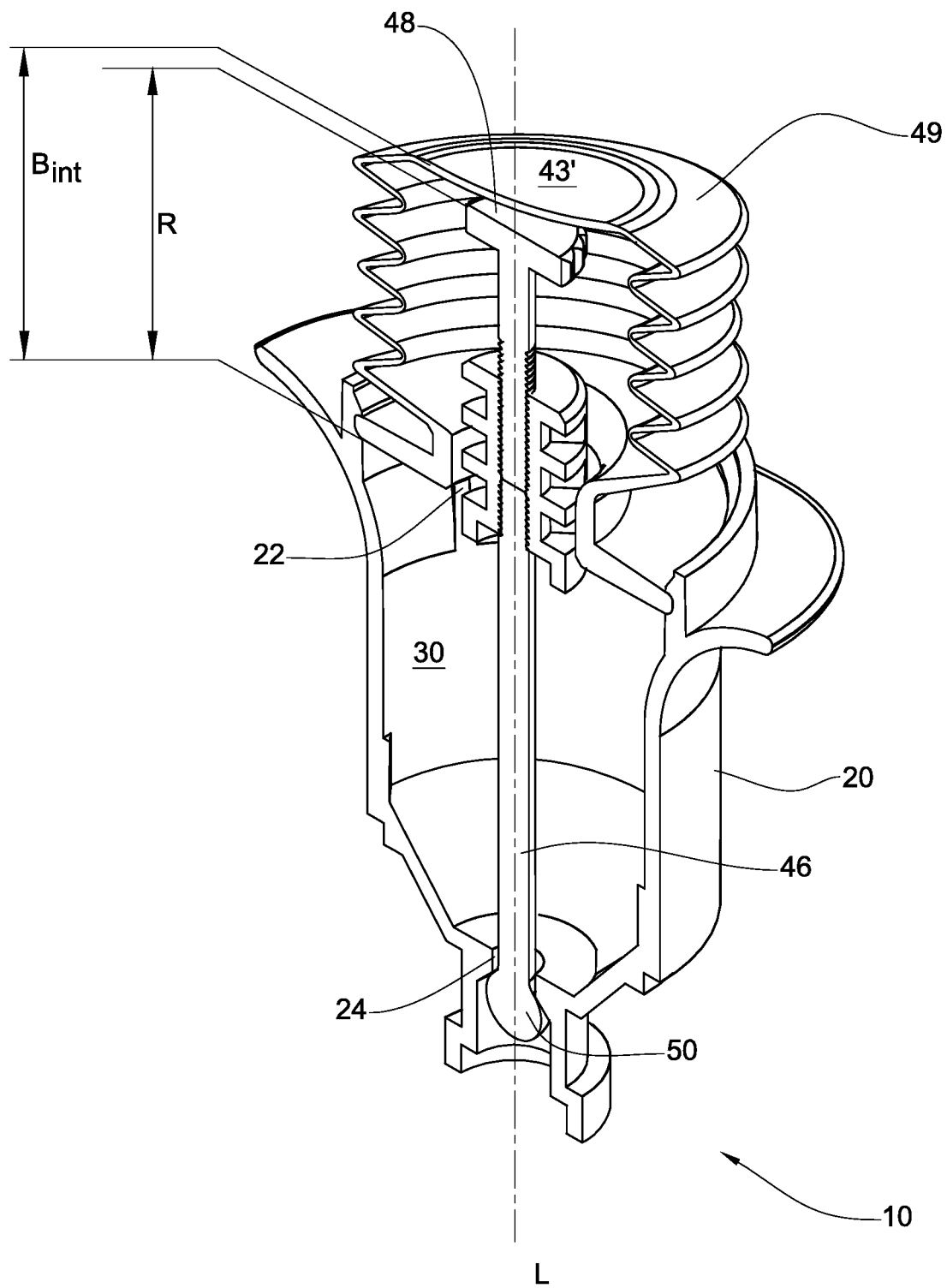
Figure 1C:
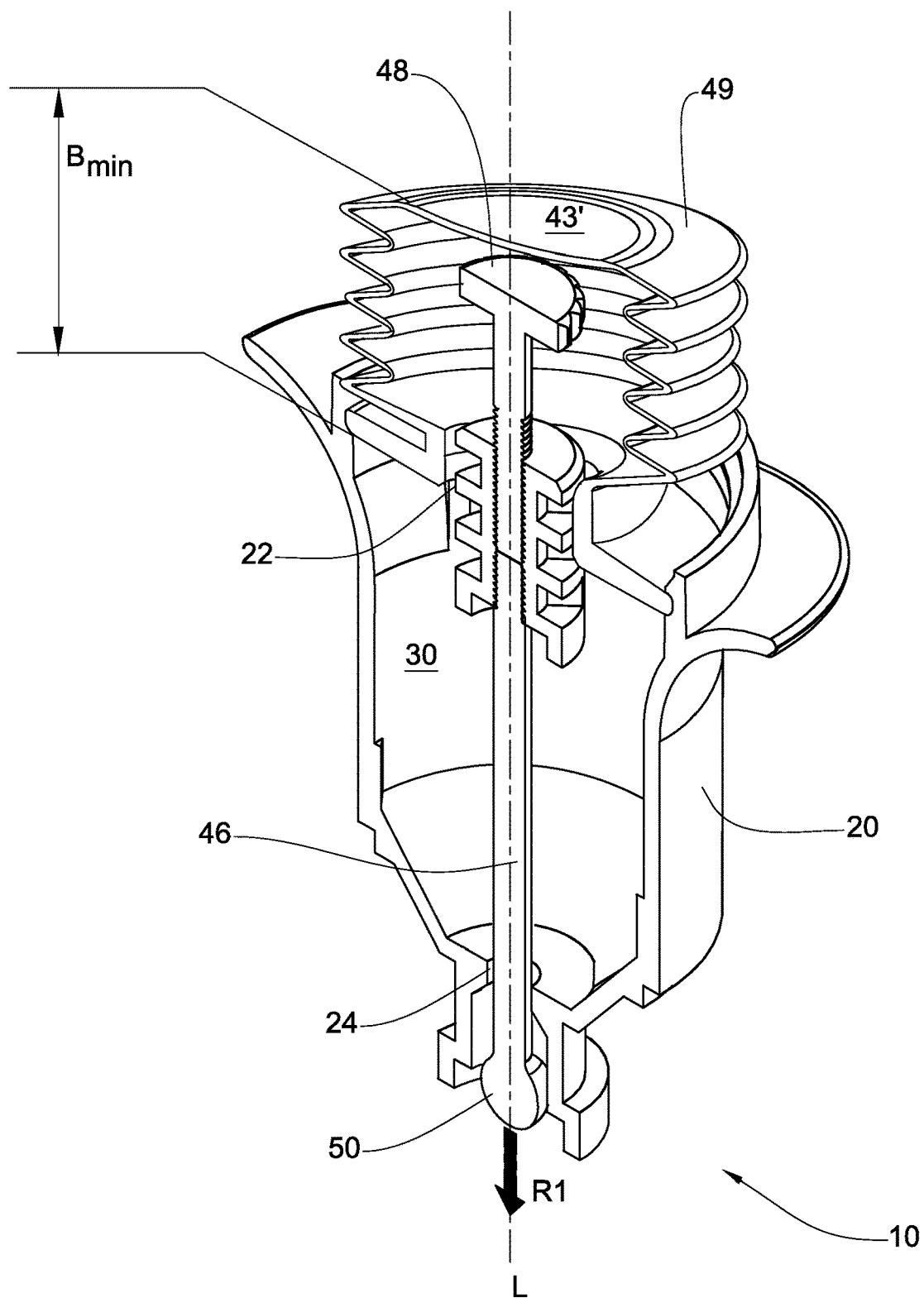

FIGS. 1A, 1B and 1C show a powder dispensing applicator 10 according to one embodiment of the presently disclosed subject matter. The powder material may be in the form of, or comprise, particulate material such as granules, microcapsules, aggregates, fibers or a mixture thereof. The powder can be composed of a single type of powder or particulate material, or a mix of powders and/or particulate material such as ORC powder, agglomerated ORC powder, gelatin particles, starch particles, gums, sugars, chitosan particles, fibrinogen particles, and thrombin particles.

The powder dispensing applicator 10 comprises a container 20 having an inlet end 21 with an inlet opening 22 and an outlet end 23 with an outlet opening 24 spaced from each other along a longitudinal axis L of the applicator 10, by a cavity 30 configured to contain a powder therein at least in the vicinity of the outlet end 23, a plug 50 configured to obstruct the outlet opening 24 for keeping it in a substantially closed state, and an actuator 40 configured to manipulate the plug 50 to bring the outlet opening 24 into its substantially open state.

In the embodiment of the applicator 10 illustrated in FIGS. 1A, 1B, and 1C, the actuator 40 comprises a deformable gas-containing actuation element 42, sealingly connected to the container 20 at the inlet end 21 thereof so that its gas containing interior is in fluid communication with the cavity 30 at least when the outlet opening 24 is to be brought from its closed state into its open state, allowing the actuation element 42, when operated manually or automatically, to introduce gas contained in element 42 into the cavity 30 through the inlet opening 22 for building up a desired pressure in the cavity 30 when the outlet opening 24 is in its closed state. The actuation element 42 thus has an initial state, in which it has a maximal amount of gas therein, and is operable to be brought into an intermediate state, in which pressure is built up in the cavity 30 when a part of the gas from the actuation element 42 is introduced into the cavity 30 via the inlet opening 22.

In addition to the ability of the actuation element 42 to be brought from its initial state into its intermediate state as described above, the actuation element 42 is configured to manipulate the plug 50, after the desired pressure has been built up in the cavity 30. More particularly, the actuation element 42 can be configured for being brought, manually or automatically, from the intermediate state, into a final state so that, while undergoing this change of state, it is configured to exert on the plug 50 an opening force causing it to move away from the cavity 30 and the outlet opening 24 in the direction R1, as indicated in FIG. 1C.

In some embodiment, the plug 50 is configured to be moved between an obstructing position, in which the outlet opening 24 is closed thereby, and an unobstructing position, in which the plug 50 is disposed further from the cavity 30 (or from the outlet opening 24) than in the obstructing position and in which the outlet opening 24 is thus open.

In order to exert the opening force on plug 50, the actuator 40 can further comprise a force transmitting element, e.g. such as element 46, shown in FIGS. 1A, 1B, and 1C, manipulatable at least indirectly e.g. by the actuation element 42, so as to exert the opening force on the plug 50 when the actuation element 42 is brought from the intermediate state into the final state, thereby bringing the outlet opening 24 into its open state.

In the applicator 10 shown in FIG. 1A, the actuation element 42 is in the form of a bellows 49 having a closed proximal end 43', an open distal end 43" defining the inlet opening 22 at its area close to the axis L and a bellows interior void 39 therebetween. The bellows 49 is sealingly fixed to the container 20 at its area radially spaced from the inlet opening 22. The force transmitting element of the applicator 10 shown in FIG. 1A is in the form of a rod 46 passing through the inlet opening 22 and the outlet opening 24 and having its proximal end 48 within the interior void 39 of the bellows 49 and its distal end with the plug 50 disposed distally with respect to the outlet opening 24. FIG. 1A shows the bellows 49 and the rod 46 in their initial states, in which the bellows 49 has a maximal volume and/or amount of gas, such as air, within its interior void 39, and a maximal distance Bmax between its proximal end 43' and the inlet opening 22, and the rod 46 has its proximal end 48 at a distance R from the inlet opening 22, and the plug 50 located at the distal end of the rod disposed at a location abutting and obstructing the outlet opening 24, defining the closed state of the outlet opening 24.

It will be appreciated that the rod 46 and the plug 50 shown in FIGS. 1A, 1B, and 1C can be assembled together from separate units, or constructed as a monolithic unit.

FIG. 1B shows the applicator 10 with the bellows 49 in its intermediate state, and with the plug 50 staying in its obstructing position defining the closed state of the outlet opening 24. To bring the bellows 49 into this state, it has to be axially pressed at its proximal end 43' thereof, e.g. manually by a thumb (not shown) of a user, and compressed so that its proximal end 43' moves to a distance Bint from the inlet opening 22, causing a part of the gas to flow from the interior void 39 of the bellows into the cavity 30 via the inlet opening 22. Since the plug 50 maintains its obstructing position, closing off outlet opening 24 of cavity 30, and inlet end 21 of cavity 30 is closed off by the sealed connection with bellows 49, which is itself closed, the introduction of gas from the interior void 39 of the bellows 49 into the cavity 30 causes a pressure within the cavity to be built up. The distance Bint is selected so as to be not shorter than the distance R to make sure that the proximal end 43' of the bellows 49 does not exert any force on the proximal end 48 of the rod 46, and does not cause the rod 46 to move the plug 50 away from the outlet opening 24 until the pressure built up in the cavity 30 reaches a predetermined value.

It will be appreciated that the amount of pressure built up in the cavity 30 as described above can be a function of one or more of the physical and configurational parameters of the applicator 10, e.g., the ratio between Bmax and R, the ratio between the volume of the cavity 30 and the interior void 39 of the actuation element 42, etc. For example, in the applicator 10, Bmax could be between 2.3 to 2.7 times the length of R, and the volume of cavity 30 could be between 1 and 1.3 times the volume of the interior void 39 of the actuation element 42.

In another example, the length of element 46 can be decreased or increased so as to change the dimension R, the extent to which the element 46 extends into the interior void 39 of the actuation element 42, in order to control the pressure built up in cavity 30 prior to its release.

It will further be appreciated that pressure can be built up in the cavity 30 as described above, even while the connection between actuation element 42 and container 20 is not completely sealed to gas.

It will be appreciated that in FIGS. 1A-1C and the description provided above, the initial, intermediate and final states of the actuation element 42 are presented as distinctive states in order to describe in clear detail how the applicator 10 works. However, it is to be understood that in ordinary operation of the actuation element 42 of the applicator 10, its above states can be taken successively and continuously, i.e. without any intervals therebetween, by pressing the actuator in one movement which can be as rapid as desired.

It will further be appreciated that in the applicator of the presently disclosed subject matter, alternative means of gas compression, such as a shape memory elastic bulb, or a piston within a cylinder, can be used in place of a bellows, such as that illustrated in FIG. 1.

Continued axial pressing (distally) on the proximal end 43' of the bellows 49 causes the bellows, as shown in FIG. 1C, to push distally the proximal end 48 of the rod 46 and to move therewith towards the inlet opening 22, whereby the bellows 49 reaches its final state characterized by the minimal spacing Bmin of the proximal end 43' of the bellows 42 from the inlet opening 22, and by the minimal amount of gas in the interior void 39 of the bellows 49. It is noted that a small space appears in FIG. 1C between proximal end 43' of the bellows 49 and proximal end 48 of the rod 46 for the sake of clarity of the parts in the illustration only, and that as described above, proximal ends 43' and 48 of the bellows 49 and the rod 46 respectively, should be considered to be in contact with one another when the bellows is in its final state.

When the rod 46 is pushed distally by the proximal end 43' of the bellows 49, the rod exerts on the plug 50 the opening force, directed along longitudinal axis L away from the cavity 30, thereby moving plug 50 away from the outlet opening 24 into its unobstructing position, thus bringing the outlet opening 24 into the open state.

The fact that prior to opening the outlet opening 24, the pressure has been built up in the cavity 30 to a pressure P1, leads to the creation of a pressure differential between that within the cavity 30 and the outside atmosphere (atm) (i.e., $P1 > P_{atm}$), such that when the outlet opening 24 is opened, a pressurized gas flow is generated out of the outlet opening 24. When the cavity 30 contains a powder therein at least in the vicinity of the outlet opening 24, this pressurized gas flow causes at least a portion of the powder, i.e. a powder dose, to be propelled out of the outlet opening in a pressurized burst.

Thus, during the movement of plug 50 away from its obstructing position into its unobstructing position, the powder contained in the applicator is dispensed.

In one example of an applicator 10 having an initial bellows volume of 10 ml in the initial state, and a final bellows volume of 5 ml in the final state, in accordance with the presently disclosed subject matter, the pressure in cavity 30 could reach a pressure of between 1.1 and 3 atm such as 1.25, 1.45 atm just prior to opening of outlet opening 24.

It will be appreciated that this pressure is built up inside the applicator provided in accordance with the presently disclosed subject matter without an external pressurized gas source.

It will be appreciated that one advantage of the pressurized burst of powder released from applicator 10 in accordance with the presently disclosed subject matter is the precise application of the powder dose on a target location, in an accurate and consistent distribution, since the powder is released from the outlet opening 24 in a pressurized burst of spray which creates a focused aerosol and powder spots on the target location.

It will further be appreciated that an additional advantage of the pressurized burst of powder released from applicator 10 in accordance with the presently disclosed subject matter is that it allows the powder burst to be directed in any possible direction including the horizontal direction as well as the vertical upward direction, i.e. against the force of gravity, since the powder disposed in the cavity at least in the vicinity of the outlet opening is propelled as a spray from outlet opening 24 with kinetic energy and has its own momentum, allowing it to travel some distance before being counteracted by gravity. It will further be appreciated that the powder can be applied even while the orientation of the applicator itself its changing, from the vertical to the horizontal, upwards, downwards and every angle in between.

The freedom to spray powder without restrictions enables the applicator to be used more intuitively by a user. Furthermore, access to otherwise difficult to reach locations is allowed.

It will further be appreciated that the applicator provided in accordance with the presently disclosed subject matter can be configured such that the distance which the plug 50 is moved away from the outlet opening 24 can be increased such as to effectively increase the area in the vicinity of outlet opening 24 which is unobstructed by plug 50, thereby reducing the velocity of the gas and powder flow exiting the applicator.

In another embodiment, the actuator 40 can further comprise a force exerting element configured to manipulate at least indirectly the force transmitting element 46 so as exert on the plug 50, a closing force. The closing force is directed along the longitudinal axis L towards cavity 30 and brings the plug 50 into the obstructing position from the unobstructing position, when the opening force is terminated, and it maintains the plug 50 in the obstructing position until the opening force is exerted.

Figure 2A:
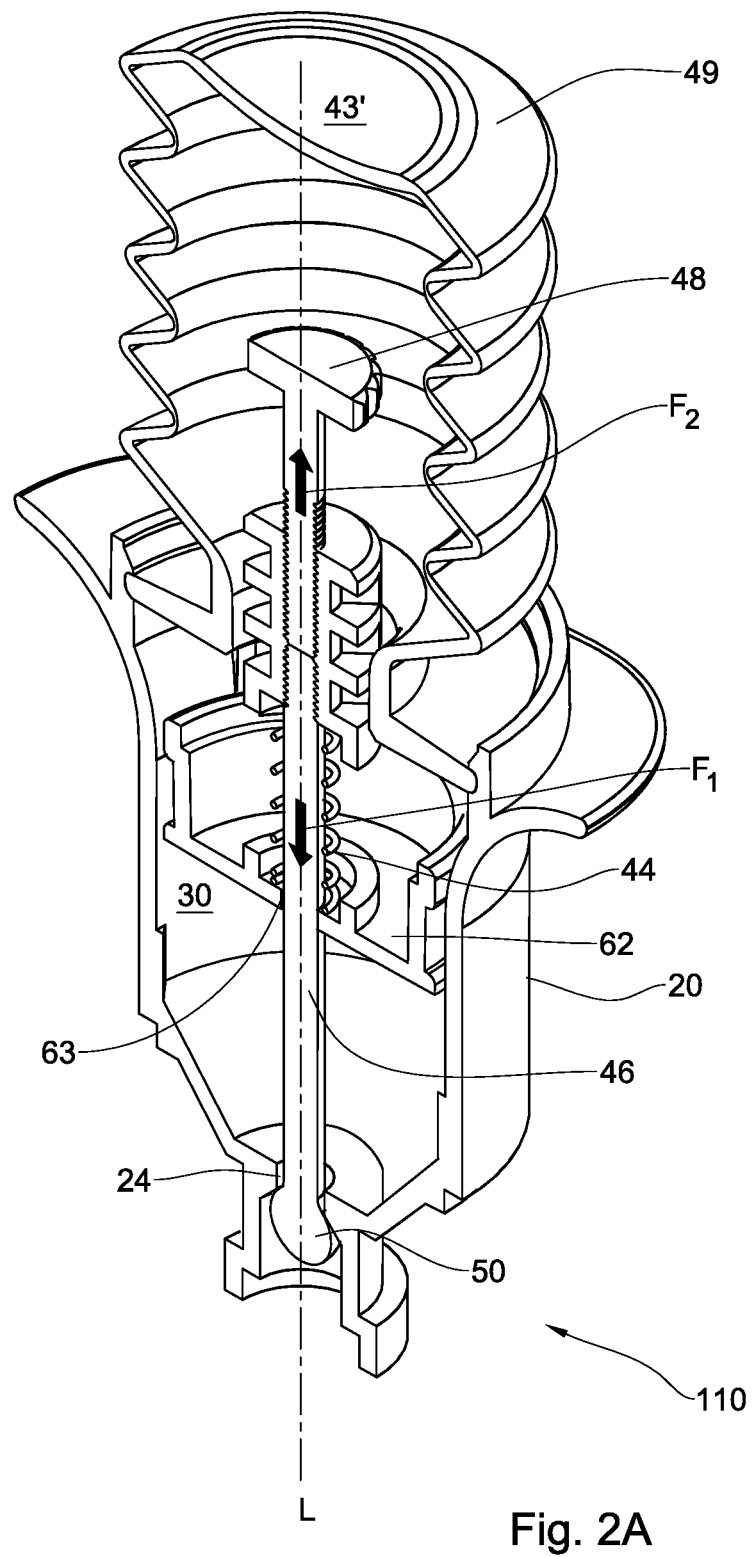
FIGS. 2A and 2B are schematic perspective illustrations of a powder dispensing applicator, in accordance with a further example of the presently disclosed subject matter, with its outlet opening in a closed and open state, respectively.
Figure 2B:
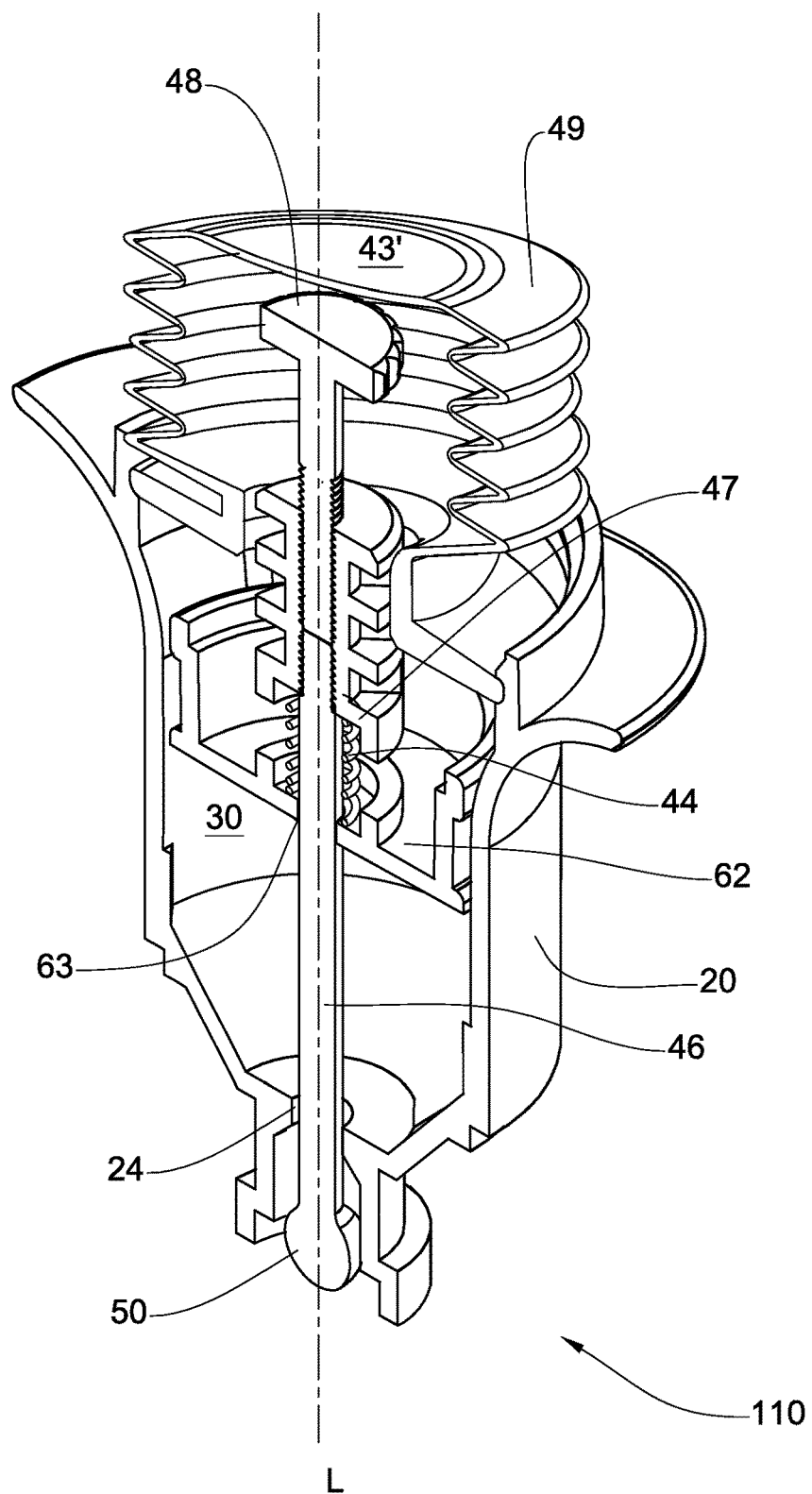
Figure 3A:
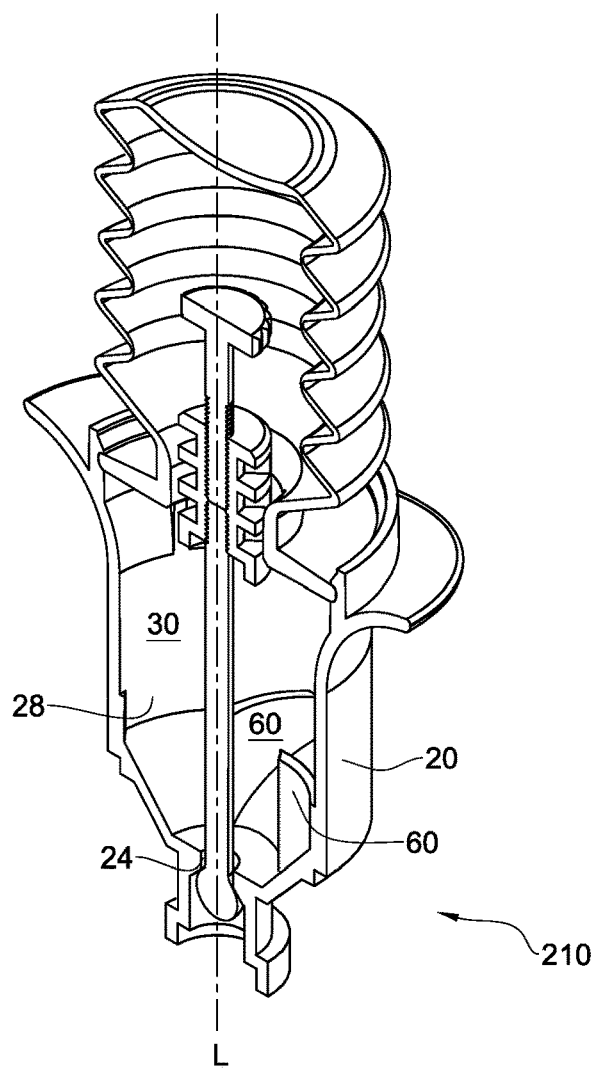
FIG. 3A is a schematic perspective illustration of a powder dispensing applicator, in accordance with a still further example of the presently disclosed subject matter, having internal ribs.
Figure 3B:
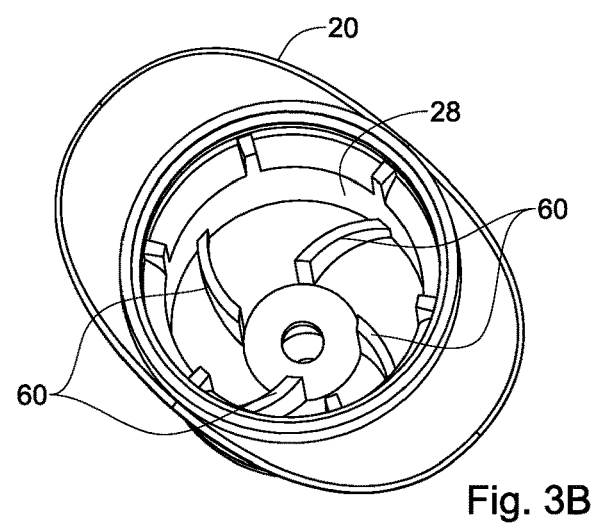
FIG. 3B is a top view of a container of the applicator shown in FIG. 3A.

One example of an applicator having such a force exerting element is shown in FIGS. 2A and 2B and is designated as 110. The applicator 110 has the same components, and is operated in the same manner as the applicator 10 shown in FIGS. 1A, 1B and 1C, and it differs from the applicator 10 in that it has the above mentioned force exerting element, which in the applicator 110 is in the form of a spring, designated 44 in FIGS. 2A and 2B. The spring 44 is configured to be brought into a compressed state when the force transmitting element 46 exerts the opening force on the plug 50 to bring it into the unobstructing position (FIG. 2B), and an extended state, in which the force transmitting element 46 exerts on the plug 50 the closing force, to bring the plug 50 into the obstructing position (FIG. 2A).

The spring is furthermore configured to be maintained in its partially extended or extended state until the deformable gas-containing actuation element 42 is brought into the intermediate state from its initial state, and to be compressed at least indirectly by the deformable gas-containing actuation element 42 when it is brought from the intermediate state into the final state.

In the applicator 110, in order for spring 44 to be held within the container 20 so as to be compressible when the bellows 42 exerts directly or indirectly on the plug 50 the opening force, there is provided in the cavity 30, a proximal spring seat 47 held by the rod 46 and movable therewith by the actuation element 42, and distal spring seat 62 fixed to the inner surface of the container 20. The proximal spring seat 47 can constitute a unitary body with the rod 46 or can be assembled therewith at a location disposed distally to its proximal end 48 but closer to this extremity than to the distal spring seat 62, along longitudinal axis L of applicator 110. The distal spring seat 62 can be formed as a unitary body with the container 20 or can be assembled therewith, and it can have a central passage 63 configured to surround the rod 46 allowing its free movement therealong, when moving the plug 50 between its positions corresponding to the open and closed states of the outlet opening 24.

The spring 44 is brought into its compressed state by the actuation element 42, when the actuation element 42 applies to the rod 46 with the plug 50, the distally pushing, opening force, shown in FIG. 2A as force F1, thereby moving distally the proximal spring seat 47. This seat 47 then exerts on the spring 44, which abuts the fixed distal spring seat 62, a force $F_s = -k\Delta x$, where k is the spring constant and $\Delta x$ is the distance through which the spring is compressed. When the opening, distally pushing force is terminated, the spring 44 tends to expand, thereby exerting on the rod 46 with the plug 50, via the proximal spring seat 47, the closing, proximally pulling force, shown in FIG. 2A as force F2, causing the plug 50 to return to obstruct the outlet opening 24 and keep it in its closed state as long as no opening, distally pushing force is exerted on the plug 50. This closed state characterizes the default state of the applicator 110, which is maintained at all times except when the actuation element 42 is operated to be brought from its intermediate into its final state by the user's pressing thereon until the opening, distally pushing force is exerted on the plug 50, whereby the unintentional powder release out of the applicator due to gravity or occasional movement is prevented.

An additional advantage of the applicator 110 being in the closed position by default, is that the applicator is thus always in a ready-to-use position. The applicator 110 can thus be immediately operated to express powder, without any requirement for the user to first activate it, e.g., to change its mode from 'off' to 'on'. This increases the user-friendliness of the applicator, making it more intuitive to use, and thereby helping to prevent confusion during use that can hinder smooth operation of the applicator.

It will further be appreciated that since the applicator returns to a ready-to-use position after each use, repeated dosing is enabled. In a configuration of applicator 110 in which only a portion of the powder in cavity 30 is used in each dose, the applicator can be used repeatedly until the powder in cavity 30 is all used up, thus maximizing the percentage of powder provided in the applicator which is ultimately used, and minimizing the wastage of powder.

It will be appreciated still further, that pressure is built up in cavity 30 for each use of the applicator, so that each sequential dose in a series of doses provides all the benefits provided in the initial dose without any reduction in efficacy, i.e., powder application is achieved via a pressurized burst in the manner described above in each and every application. In the example of applicator 110, after the user desists from pressing on proximal end 43' of the bellows 42, and the spring 44 exerts the closing force as described above to move the plug 50 from the unobstructing position into the obstructing position, the deformable gas-containing actuation element 42 draws ambient air into its interior void 39, thus returning it from its final state to its initial state, in which state it is ready again for operation to deliver the next pressurized dose of powder.

When the deformable gas-containing actuation element 42 is released, it returns to its original volume, resulting in a decrease of pressure in the interior void 39, a flow of ambient air into the interior void 39 and pressure equilibration. The flow of ambient air into the interior void 39, can occur via the outlet opening 24 until it becomes closed and/or via interstitial spaces between components of the applicator, which can be not completely sealed to gas, as mentioned previously with respect to the connection between the actuator 42 and the container 20.

In one embodiment, the deformable gas-containing actuation element 42 can be configured with an opening, for example, in the closed proximal end 43' of bellows 49. During operation, this opening can be sealed by the thumb of the user during the pressing of the bellows 49 when it is compressed from its initial state to its final state. The release of the thumb from the bellows then allows ambient air to flow into the interior void 39 due to the pressure differential formed as plug 50 moves back to its obstructing position at outlet opening 24 and bellows 49 returns from its from its final state to its initial state.

It is also clarified that in general the extended state of the spring 44 can be actually a partially compressed state of the spring, with respect to its physical parameters, as it is configured in accordance with the presently disclosed subject matter to exert the closing force in this state, which is provided by the potential energy of its partially compressed status as explained above, however, this partially compressed state is an extended state with respect to the relatively more compressed state of spring 44 shown in FIG. 2B.

It is also clarified that in general the compressed state of the spring 44 can be actually a partially extended state of the spring, with respect to its physical parameters, as it is configured in accordance with the presently disclosed subject matter to be compressed to some extent by the opening force exerted by the user which moves the plug 50 into its unobstructing position via the rod 46 which passes through the spring 44, however, this partially extended state is a compressed state with respect to the relatively more extended state of spring 44 shown in FIG. 2A.

Any of the applicators 10 and 110 described above, as well as any other applicator according to the presently disclosed subject matter, which has a cavity similar to the cavity 30, can comprise at least one internal element disposed within the cavity 30, configured to introduce turbulence into the flow of gas when propelling at least a portion of the powder out of the outlet opening. Such turbulence can be advantageous at least for reducing the amount of residual powder that can be left in the cavity 30 after the use of the applicator. The turbulence can further be advantageous for achieving a more uniform suspension of the powder in the gas.

The internal element can be at least one rib, which can have any appropriate shape such as, e.g., a blade-like shape. An example of an applicator which has the above internal element, and in addition has the same features as the applicator 10, is shown in FIGS. 3A and 3B, where the applicator is designated as 210, an inner wall of the container 20 is designated as 28 and the blade-like ribs protruding from the inner wall 28 into the cavity 30, are designated as 60.

When a laminar flow of gas entering cavity 30 from the actuation element 42 impinges upon the ribs 60, the direction of the flow of gas is shifted toward the inner wall 28 while moving distally. This can have a sweeping effect on particles of powder positioned close to, or clinging to the inner wall 28, such that these particles are propelled out of outlet opening 24, rather than remaining in the applicator 10 and not being used. Thus, the greatest possible percentage of the total volume of the powder in the applicator is more likely to be used, i.e., propelled through outlet opening 24 during the operation of applicator 210, rather than remaining inside the cavity 30 and being wasted. In the event that the total volume of the powder in the applicator 10 is a single dose, this can prevent the application of an insufficient or inaccurate dose.

It will be appreciated that the rib 60 can be of any shape and any size such that it creates turbulence in cavity 30. For example, the rib 60 can have a radial extension of between not less than 0.25 R and not greater 0.75 R, where R is an average distance between the inner wall 28 and the longitudinal axis L. An exemplary axial extension of the rib 60 could be not less than 0.5 H, wherein H is an axial extension of cavity 30.

It will further be appreciated that, in order to further optimize the mix of the gas and the powder in the cavity 30 so as to achieve maximal delivery of powder out of the applicator, the cavity 30 can be filled with powder so that the powder occupies up to 85-90% of the total free volume of the cavity 30, so as to leave a void space in the cavity free from powder.

Figure 4:
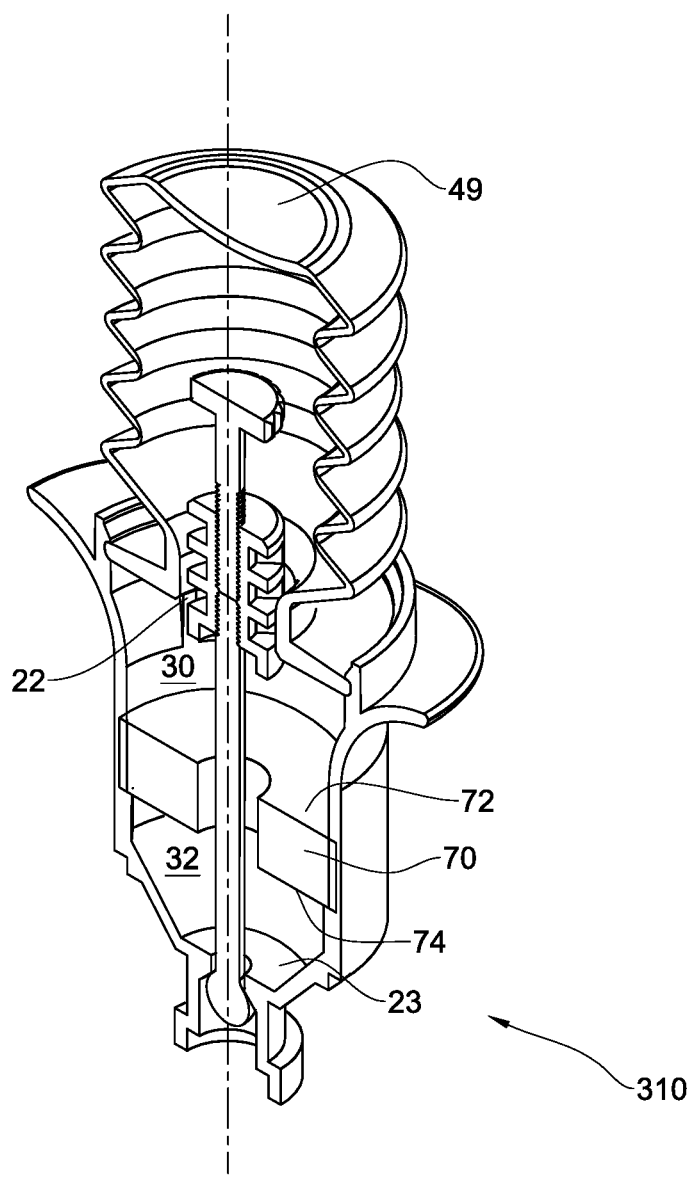
FIG. 4 is a schematic perspective illustration of a powder dispensing applicator, in accordance with a still further example of the presently disclosed subject matter, having a filter.
Figure 5:
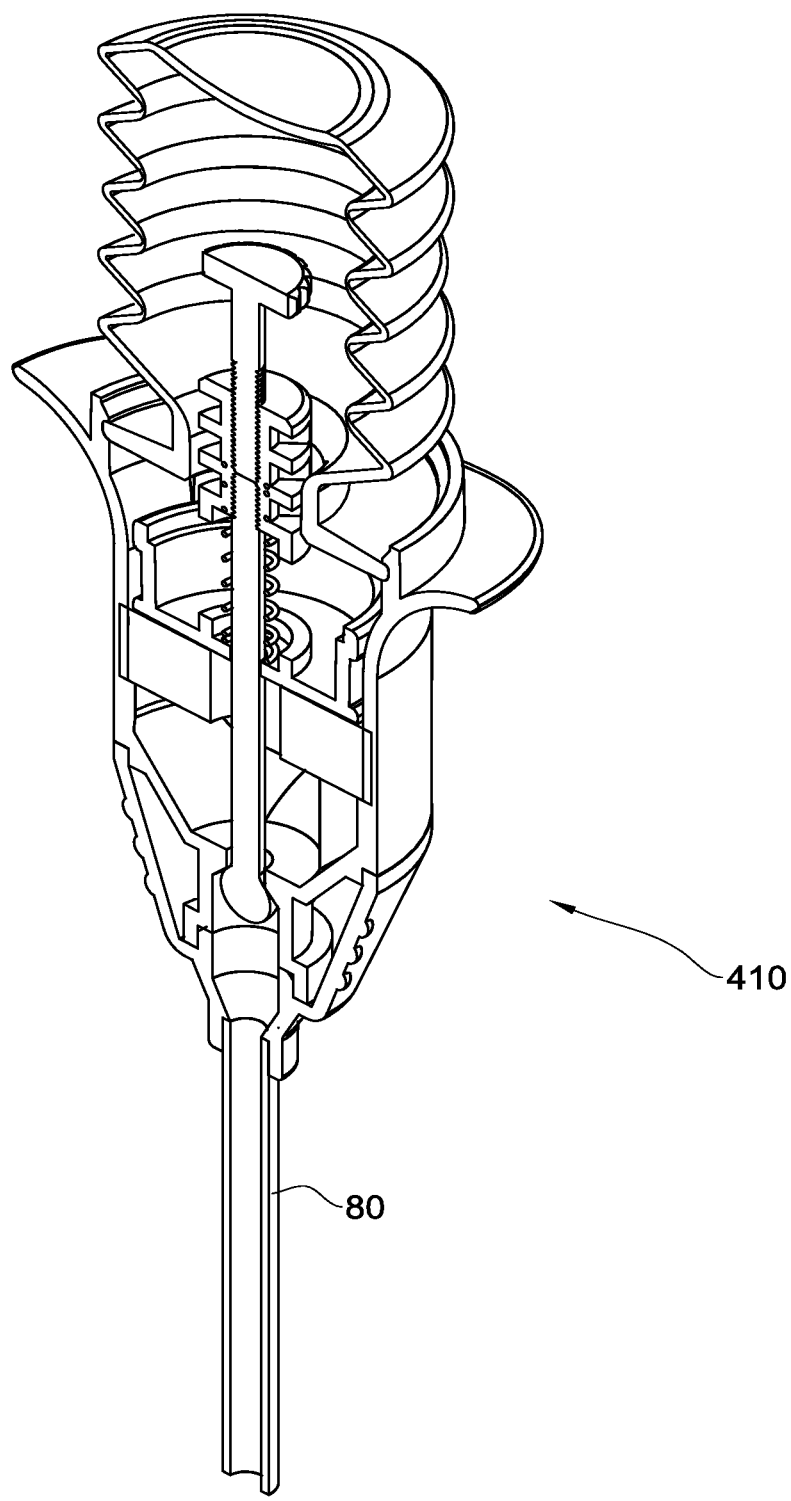
FIG. 5 is a schematic perspective illustration of a powder dispensing applicator, in accordance with a still further example of the presently disclosed subject matter, having all of the elements of the exemplary applicators shown in FIGS. 1A-1C, 2A-B, 3A and 4, with suitable modifications, where required, as well as a disposable applicator tip.

Any of the applicators 10, 110 and 210 described above, or any other similar applicator according to the presently disclosed subject matter, can comprise a gas-permeable filter fitted within the cavity 30 adjacent to the inlet opening 22 so as to prevent the powder from moving from the cavity 30 into the actuation element 42 through the inlet opening 22, but to allow gas entering the cavity 30 from the actuation element 42 through the inlet opening 22, to pass through the filter (and only through the filter) towards the outlet end 23 of the container. The filter can have a first side facing the inlet opening 22 and a second side facing the outlet end 23 of the container 20 and can be disposed so as to create a chamber for the powder between the second side of the filter and the outlet end 23 of the container. An example of an applicator which has the above filter and in addition has the same features as the applicator 10, is shown in FIG. 4, where the applicator is designated as 310, the filter is designated as 70, its first side is designated as 72, its second side is designated as 74 and the chamber is designated as 32.

It will be appreciated that the filter provided in the presently disclosed subject matter can be affixed by any suitable means to the interior of the container 20, e.g. to the inner wall 28 of the cavity 30, and thus not rest directly on the powder contained in the applicator, and therefore not apply any force on the powder. Aggregation, agglomeration and caking of the powder is thus prevented.

In all of the above described applicators, the outlet end 23 of the container 20 is shown to have an axially extending outlet port 41 having the outlet opening 24 at its proximal end and a plug passage 55 extending distally from the outlet opening 24 so as to allow the plug 50 to move therealong from its proximal position, in which it abuts and obstructs the outlet opening 24, into its distal position, in which it does not obstruct it, being distally spaced therefrom along the passage 55. The plug 50 is shown to have such a cross-sectional shape as to be larger than the outlet opening 24 in at least one cross-sectional dimension in order to prevent axial movement of the plug 50 in the proximal direction, when the outlet opening 24 is in its closed state. The passage 55 can have such cross-sectional shape along its length spaced from the outlet opening 24 as to allow the plug to move freely therealong away and towards the outlet opening 24 when bringing it into its respective open and closed states.

For example, plug passage 55 can have passage internal walls 56 such as shown in FIG. 1A. Plug 50 can be disposed between the passage inner walls 56 when in its obstructing position, and it can be moved away from the passage inner walls 56 when it is moved into its unobstructing position.

As further shown in FIG. 1A, the plug 50 has a maximal cross-sectional dimension Dplug, the outlet opening 24 has a corresponding cross-sectional dimension d, which is smaller than Dplug, and the passage 55 has a corresponding cross-sectional dimension Dpass, which is greater than Dplug and which varies along the axis L. In all the applicators described above, the cross-sectional shape of the plug 50, the outlet opening 24 and the passage 55 is circular, and the above indicated dimensions are their corresponding diameters. However, in the above applicators as well as in any other applicators according to the presently disclosed subject matter, any one of the plug, the passage 55 and the outlet opening can have any other irregular or regular cross-sectional shape such as, e.g. oval or polygonal, in which case the above dimensions will be the diameters of circles inscribed in that shape.

In any of the above described applicators or any other similar applicator according to the presently disclosed subject matter, in some embodiments, the plug 50 can be configured to obstruct only partially the outlet opening 24 when bringing it into the closed state so as to prevent the powder from exiting the outlet opening 24, while allowing some amount of gas to pass through the outlet opening 24. In this case, an extent of the partial obstruction of the outlet opening 24 by the plug 50 should be such as to still allow the pressure differential to be generated as described above, to propel the pressurized burst of powder out of the outlet opening 24. In any of the above described applicators or any other similar applicator according to the presently disclosed subject matter, in some embodiments, the outlet opening 24 is "closed" for powder but not completely closed for gas. In such embodiment, although the plug is not completely air tight, a pressure differential can be generated.

An applicator according to the presently disclosed subject matter can comprise all or only a part of the features of the applicators 10, 110, 210 and 310 described above. An applicator 410 comprising all of these features is shown in FIG. 5. In the applicator 410 shown in FIG. 5, distal spring seat 62 has been modified to include filter-holding appendages (not seen).

An applicator according to the presently disclosed subject matter can comprise additional features not disclosed herein.

In any applicator according to the presently disclosed subject matter an applicator tip, such as applicator tip 80 shown in FIG. 5, can be used. The applicator tip can be connected to a hub which is configured to be snap-fitted onto the container 20 of applicator 10 at its distal end, near outlet opening 24, allowing the applicator tip 80 to be exchanged as required, e.g. for exchanging a short applicator tip with a long one in accordance with the application requirements. For example, it can be desirable to use a tip with a long length for minimally invasive procedures.

It will be appreciated that applicator tips with long lengths can be advantageously used with applicator 10, in that robust powder application can still be provided even when the powder is forced to travel the full length of a long applicator tip before being expelled onto the target location, due to the kinetic energy imparted to the powder spray in the pressurized burst from the applicator provided in accordance with the presently disclosed subject matter.

The applicator tip 80 can be made of material such as polymer, metal or a combination of the two, and can be rigid, flexible, semi-flexible, or have shape memory. The bellows 49 can be made out of shape memory material such as plastic resin.

Container 20 can have protrusions to facilitate a good grip of the applicator with two fingers, while a third finger is used to press the actuation element 42.

In one embodiment, the applicator of this invention can contain powder to be used in a surgical scenario.

In one embodiment, the applicator can be disassembled and filled with powder by an end user.

The applicator can be comprised of material stable to gamma or eBeam irradiation.

It will be appreciated that the applicator of the presently disclosed subject matter can have a design or structure which is different from the examples shown in the figures.

For example, the applicator can be constructed with elastic material taking the place of the spring 44.

In another example, the applicator can be constructed such that the plug 50 is pulled into cavity 30 rather than pushed out of cavity 30 in order to bring outlet opening 24 into the open state.

In another example, the applicator can be constructed such that spring 44 is configured to be maintained in a partially compressed or compressed state, and to expand during the operation of the applicator, such that after application of the powder, the tendency of the spring 44 to contract exerts the closing force on the plug 50 to bring outlet opening 24 into the closed state.

In another example, the applicator can be constructed such that the opening and closing forces exerted to move the plug at least indirectly can be exerted by bands, strings, gears or a rod in combination with gears.

In another example, the gas pressure buildup can take place inside the actuation element 42 and not in the cavity 30.

The applicator can be constructed in such a way that in its inoperative state, there is no fluid communication between the deformable gas-containing actuation element 42 and the cavity 30. For example, a seal can be located at inlet opening 22, such that when the actuation element 42 is operated, pressure can build up in the actuation element 42 rather than in the cavity 30. The seal could then be ruptured, when pressure in the actuation element 42 reaches a predetermined value, or by mechanical means. At the same time, outlet opening 24 can be opened, either as a result of the buildup of pressure, or by mechanical means, and the powder can be propelled out of the applicator in a pressurized burst.

In an embodiment of the applicator having a seal as described above which can be ruptured when the applicator is used for the first time, the applicator can be used as a disposable applicator.

It will be appreciated that in one embodiment, the mechanism by which the outlet opening 24 is opened is independent of the pressurized gas. In another embodiment, the release of pressurized gas is carried out by a mechanism which is independent of pressurized gas, for example, by mechanical means (such as by pressing proximal end 48 of rod 46.)

The invention claimed is:

1. A powder dispensing applicator comprising:
a container having an inlet opening and an outlet opening spaced from each other along a longitudinal axis (L) of said applicator by a cavity configured to contain a powder therein at least in the vicinity of said outlet opening when the outlet opening is in a closed state and to allow at least a part of the powder to be expelled therefrom when the outlet opening is in an open state;
an actuator comprising a deformable actuation element configured to contain a gas therein and to be brought from its initial state, in which it has a maximal operational volume, into a final state in which it has a minimal operational volume, via an intermediate state, in which it has an intermediate operational volume smaller than the maximal volume, for building up pressure in said applicator when the outlet opening is in its closed state; and further configured for being brought from its final state into its initial state by drawing ambient gas thereto from an exterior of the applicator after the built-up pressure is released, wherein the actuation element is in the form of a bellows or a shape memory elastic bulb having a closed proximal end, an open distal end defining the inlet opening at its area close to the axis L, and an interior void therebetween; the bellows or the shape memory elastic bulb being sealingly fixed to the container at its area radially spaced from the inlet opening; wherein the actuator further comprises at least one force transmitting element passing through the inlet opening and the outlet opening and having its proximal end within the interior void of the bellows or the shape memory elastic bulb, a plug which is the distal end of the force transmitting element, the plug being disposed distally with respect to the outlet opening, wherein the plug is configured to obstruct the outlet opening for keeping it in the closed state until said plug is operated by the actuator to bring the outlet opening into the open state when the actuation element is brought from the intermediate state into the final state, to create a flow of said gas generated due to a pressure differential between that within the applicator and that at its exterior, for propelling therewith at least a portion of the powder out of the outlet opening in a pressurized burst;

a gas-permeable filter having a first side facing the inlet opening and a second side facing the outlet opening, and disposed in the cavity so as to create between the second side of the filter and the outlet opening a chamber for the powder, the filter being configured to form a barrier to said powder for preventing the powder from moving through the filter towards the inlet opening, and wherein:

(i) the plug is configured to be moved between an obstructing position, in which the outlet opening is closed thereby, and an unobstructing position, in which the plug is moved away from the outlet opening and is thus open;

(ii) the actuator is configured to selectively exert on the plug:

an opening force directed along said axis (L) to move the plug from the obstructing position into the unobstructing position; and a closing force directed along said axis to bring the plug into the obstructing position from the unobstructing position, when the opening force is terminated, and maintain it in this position until the opening force is exerted, one of the opening and closing forces being directed towards the cavity and the other one of these forces being directed away from the cavity;

(iii) the at least one force transmitting element is manipulatable, at least indirectly, by the deformable gas-containing actuation element, so as to exert said opening force to the plug when the deformable gas-containing actuation element is brought from the intermediate state into the final state; and wherein:

(iv) the actuator comprises at least one force exerting element configured to manipulate, at least indirectly, the force transmitting element so as to exert said closing force on the plug when the deformable gas-containing actuation element is returned from its final state to its initial state, wherein said force exerting element is in the form of a spring which is brought into a compressed state when the force transmitting element exerts the opening force on the plug to bring it into the unobstructing position, and an extended state, in which the force transmitting element exerts on the plug the closing force, to bring the plug into the obstructing position.

2. The applicator according to claim 1, wherein the outlet opening is in the form of an axially extending passage having passage inner walls, in which the plug is disposed between the passage inner walls when in its obstructing position, and from which the plug is moved away from the passage inner walls into its unobstructing position.

3. The applicator according to claim 1, wherein the spring is configured to be maintained in its extended state until the deformable gas-containing actuation element is brought into the intermediate state from its initial state, and to be compressed at least indirectly by the deformable gas-containing actuation element when it is brought from the intermediate state into the final state.

4. The applicator according to claim 1, wherein the cavity has at least one internal element configured to introduce turbulence into said flow of gas when propelling at least a portion of said powder.

5. The applicator according to claim 4, wherein said at least one internal element is at least one rib.

6. The applicator according to claim 5, wherein said container has an inner wall defining said cavity and said at least one rib protrudes inwardly from said inner wall.

7. The applicator according to claim 1, wherein said pressure is between 1.25 and 1.45 atm just before opening of said outlet opening.

8. The applicator according to claim 1, wherein said deformable gas-containing actuation element has a maximal amount of gas therein in its said initial state when it has said maximal operational volume, has a minimal amount of gas therein in its said final state when it has said minimal operational volume, and is sealingly connected to said container so as to introduce said gas into the cavity via said inlet opening along said axis (L), when being brought from the initial state into the intermediate state, for building up pressure within the cavity when the outlet opening is in its closed state.

9. The applicator according to claim 1, wherein the gas-containing actuation element is configured to draw ambient air inside it at least partially via said outlet opening and said cavity, to increase its volume from the minimal operational volume to the maximal operational volume when it is returned from its final state to its initial state.

10. The applicator according to claim 1, wherein the force exerting element is configured so that the duration of time necessary for the force exerting element to cause the plug to be brought into its obstructing position from its unobstructing position is selected so as to allow the gas-containing actuation element to increase its volume from the minimal operational volume to at least the intermediate volume before the plug obstructs the outlet opening.

* * * * *